United States Patent
Adam et al.

Patent Number: 6,050,815
Date of Patent: *Apr. 18, 2000

[54] PRECOATED DENTAL CEMENT

[75] Inventors: Randall E. Adam, Sierra Madre; James F. Forbes, Monrovia, both of Calif.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/618,438

[22] Filed: Mar. 15, 1996

[51] Int. Cl.⁷ .............................. A61K 6/083; A61C 7/16
[52] U.S. Cl. ................................................. 433/9; 433/226
[58] Field of Search ......................... 433/9, 226

[56] References Cited

U.S. PATENT DOCUMENTS

| | | | |
|---|---|---|---|
| 4,028,358 | 6/1977 | Liotta et al. | |
| 4,204,325 | 5/1980 | Kaelble | 433/9 |
| 4,407,675 | 10/1983 | Hodosh | 106/35 |
| 4,808,228 | 2/1989 | Randklev | 106/35 |
| 4,978,007 | 12/1990 | Jacobs et al. | 206/469 |
| 5,015,180 | 5/1991 | Randklev | 433/226 |
| 5,032,445 | 7/1991 | Scantlebury et al. | 433/215 |
| 5,106,304 | 4/1992 | Chronister | 106/35 |
| 5,130,347 | 7/1992 | Mitra | 522/149 |
| 5,154,762 | 10/1992 | Mitra | 106/35 |
| 5,219,283 | 6/1993 | Farzin-Nia et al. | 433/9 |
| 5,295,824 | 3/1994 | Wong | 433/9 |
| 5,558,516 | 9/1996 | Horn et al. | 433/9 |
| 5,593,303 | 1/1997 | Cohen et al. | 433/9 |

FOREIGN PATENT DOCUMENTS

WO 95/25477  9/1995  WIPO.

OTHER PUBLICATIONS

Ralph W. Phillips, M.S., D.Sc., "Dental Cements for Luting", Skinner's Science of Dental Materials, Eighth Edition, pp. 452–453.

*Primary Examiner*—Ralph A. Lewis

[57] ABSTRACT

A dental article having a lyophilic ionic cement component on at least one surface thereof. Also contemplated are methods of using a dental article having a lyophilic ionic cement component on at least one surface thereof, and methods of making such articles.

21 Claims, 1 Drawing Sheet

PRECOATED DENTAL CEMENT

FIELD OF THE INVENTION

The present invention relates to precoated dental articles, and more preferably orthodontic articles. More specifically, the present invention relates to dental articles that have been precoated with an ionic cement.

BACKGROUND OF THE INVENTION

Orthodontic brackets that have been precoated with a resin-based adhesive have been provided for some years under the name "APC™ adhesive coated bracket" by 3M Unitek. There are some challenges related to resin-based adhesives, such as shelf life under normal storage conditions. Because the resin-based adhesive is a liquid, it is inherently unstable with time. The labile nature of certain of the chemical constituents, especially the light cure chemicals, as well as the volatility of certain components lead to gradual changes in the physical properties as well as in the ability to cure when exposed to visible light. A precoated bracket that has exceeded its shelf life may lead to a bond that is weak and may spontaneously debond.

Orthodontic brackets that have been precoated with a resin-based adhesive may also have a viscosity that is higher than optimum viscosity needed during application of the bracket to the tooth. This is because the adhesive, besides its primary role of adhering the bracket to the tooth, plays a secondary role of adhering the bracket to the release liner inside the blister in which it is packaged. To prevent the bracket from drifting or lifting off the liner, the adhesive may be made thicker than ideal. This may limit its acceptability to some extent among orthodontic professionals and their staffs and also, in general, may give weaker bonds than a less viscous material.

Recently, glass ionomer cements have been made stronger by modifying them with acrylic polymers and also adding light cure chemistry as well as acrylic dark cure chemistry. This has led to materials that are usable as orthodontic bracket adhesives. The major drawback remains the necessity to mix the powder and liquid at chairside just prior to bonding. The dark cure chemistry is such that there is only a few minutes of open time before the adhesive starts to set up and must be discarded.

SUMMARY OF THE INVENTION

The present invention provides a dental article having a lyophilic ionic cement component on at least one surface thereof. Also contemplated are methods of using a dental article having a lyophilic ionic cement component on at least one surface thereof, and methods of making such articles.

DETAILED DESCRIPTION

For purposes of the present invention, a "lyophilic" ionic cement material is a liquid-attracting material. An "ionic cement" is a material useful for adhering a dental article to a tooth that cures at least in part through an ionic cement reaction. As will be discussed below, preferred ionic cements of the present invention contain ingredients that are additionally cured through a polymerization reaction. The material that is on the surface of the dental article is described as an ionic cement component because it is only a portion of the system that is traditionally described as a complete ionic cement system. To have a complete system, one generally reacts an acidic liquid with a material that is dissolvable by the liquid and which subsequently forms a matrix that binds together to form a hard mass. Thus, typical ionic cement systems are two part systems that comprise a first liquid component and a second component that when mixed form a hard mass.

The dental article having a lyophilic ionic cement component on at least one surface thereof (hereafter referred to for ease of reference as the "precoated article") offers excellent convenience to the dentist or orthodontist by eliminating the need to place the proper amount of cement on the article at the time of bonding. Clean-up is also easy since the correct amount has been factory metered onto the surface of the article, there is not the overage often experienced when buttering on the cement by hand. Because the present system utilizes cement technology, the precoated cements as described are rather insensitive to wet environments and adhere fairly well to enamel with little or no etching. Further, the precoated cements of the present invention may be formulated so that they release fluoride.

The present dental article having a precoated lyophilic ionic cement component has the benefits of an indefinite shelf life, optimum consistency, fluoride release, wet field tolerance, adhesion to unetched enamel, optional rapid chemical or dark cure as well as light cure, and ease and economy of use for bonding an entire kit of numerous articles or even of a single article.

BRIEF DESCRIPTION OF DRAWINGS

Preferred embodiments of the invention are illustrated in the accompanying schematics.

DETAILED DESCRIPTION OF THE DRAWINGS

Figure 1:
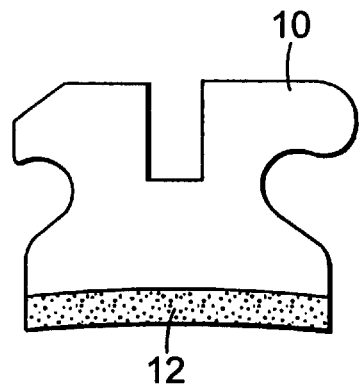
FIG. 1 is a side view of an orthodontic bracket with the cement pad adhered to the back of the bracket.

Referring now to FIG. 1, there is shown a side view of an orthodontic bracket 10 pre-coated with a dry lyophilic ionic cement component pad 12. The pad 12 is adhered to the back of bracket 10 as this is the side that must bond with the tooth. By merely wetting pad 12 with a liquid component through dipping, brushing, spraying, or some other means, a chemical reaction promptly begins, whereby pad 12 transforms into an ionic cement system which can secure bracket 10 onto the tooth surface.

Figure 2:
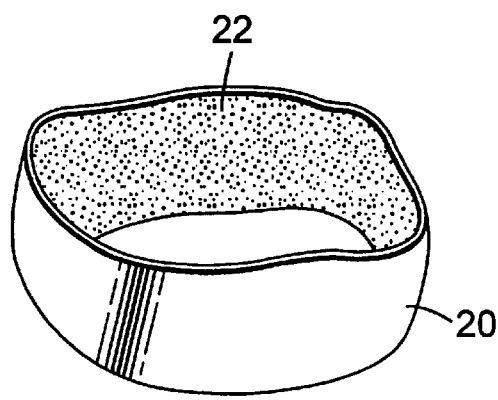
FIG. 2 is an elevation view of an orthodontic molar band with a cement pad adhered to the inner circumferential surface.

Another preferred embodiment is illustrated in FIG. 2, where a dry lyophilic ionic cement component pad 22 is pre-coated onto the inner surface of orthodontic molar band 20. Upon activation with a liquid as described above, pad 22 chemically forms into a cement system usable in securing molar band 20 around a tooth.

Figure 3:
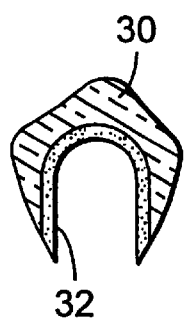
FIG. 3 is a cross-sectional view of a dental crown with a cement pad adhered to the bottom surface.

FIG. 3 is yet another preferred embodiment of the present invention, where a dry lyophilic ionic cement component pad 32 is pre-coated onto the bottom surface of a dental crown 30. Pad 32 provides a layer of ionic cement component that can be activated with a liquid, resulting in an ionic cement for bonding crown 30 to a prepared tooth.

In the present invention, traditionally dry components of ionic cement systems are placed on a surface of a dental article so as to form a lyophilic pad that is dry and thereby chemically stable. The pad of lyophilic ionic cement component should have sufficient porosity so as to allow the liquid component of the cement to flow into the pad, thereby creating an active cement composition. At the time of use, the lyophilic cement component is simply brought into contact with the liquid component of the cement so that it draws liquid into the pad. Preferably, the lyophilic pad will take up between about 10–130% of its own weight of the liquid component of the cement. More preferably the pad will take up between about 20–110% of liquid, and most preferably between about 30–90% of liquid. This measurement is taken after 5 seconds of total immersion of the pad in liquid. The incorporation of the liquid into the lyophilic cement component activates the cure mechanism, and the orthodontic article is immediately placed and pressed onto the tooth. The cure chemistry of the ionic cement may be adjusted to give rapid and strong cure, because there is no need for additional open time of the cement to allow for hand mixing as is required with traditional ionic cement systems.

Preferably, the lyophilic ionic cement is placed on the orthodontic article such that its porosity is adjusted so that it imbibes just the right amount of liquid component. The lyophilic ionic cement component powder preferably has an open, porous structure with a predetermined open volume such that when just filled, the powder:liquid ratio of the ultimate cement would be as desired. The lyophilic cement component preferably should have little or no agglomeration since a well dispersed powder is optimal in giving desired results. Also the surface characteristics of the lyophilic cement component are preferably such that the liquid fraction readily flows into the lyophilic cement component quickly and spontaneously.

The lyophilic cement component is placed on the orthodontic device in a paste or slurry, and the liquid components are removed therefrom by any suitable drying process to leave behind a dry pad of lyophilic cement component as discussed above. Preferred drying processes include simply placing the precoated orthodontic article in a dessicator, or undergoing a freeze-drying procedure. In the freeze-drying procedure, the non-liquid ingredients of an ionic cement system are dispersed in a suitable solvent, preferably in a volume fraction that is similar or identical to the volume fraction that is desired in the final bonding cement. The resulting paste is placed on the orthodontic article surface in a metered amount and the coated pad subjected to freeze drying conditions. The solvent is evaporated, but the thus lyophilized ionic cement component is prevented from collapsing onto itself by virtue of the fact that evaporating solvent remains a solid throughout the freeze-dry process. The preferred product so made is an orthodontic article having a lyophilized ionic cement component adhered thereto, wherein the lyophilized ionic cement component has essentially the appropriate open volume such that, when filled with liquid component, would have the desired powder:liquid ratio. Furthermore, by choosing the chemical identity of the solvent used to disperse the ionic cement component, the surface properties would be altered such that it would be easily wet by liquids resembling the solvent in polarity, etc. A solvent with properties near to those of the liquid component of the ultimate cement would optimize the subsequent wetting by the liquid component when the cement is activated. Preferred solvents include water and lower alcohols, such as ethanol, isopropanol, and t-butanol.

The cement as applied before lyophillization preferably has the same general characteristics as the reconstituted cement will have immediately before application to the tooth. Thus, the viscosity of the cement when in the paste form as applied to the dental article will preferably be about the same as when the precoated device is applied to the tooth. Dental articles, such as orthodontic brackets, may therefore be provided by the manufacturer any preselected cement consistency by selection of the powder:liquid ratio of the original paste as used in the coating and freeze drying process. Manufacturers may therefore provide the same bracket style in a number of cement paste consistencies. For purposes of the present invention, a paste is defined as a material wherein the inelastic modulus is less than the elastic modulus of the material. Preferably, the paste has a viscosity between about $1\times10^2$ and $1\times10^{11}$ Cps. More preferably, the paste has a viscosity between about $1\times10^7$ and $1\times10^9$ Cps. Viscosity is measured using a rheometer at a shear rate between 0.01 and 0.1 $\sec^{-1}$ at about 25° C. A preferred test protocol is to utilize a Bohlin CS50 controlled stress rheometer (Metric Group, Inc., Bohlin Instruments Division, Cranbury, N.J.) with 20 mm parallel plates and a gap of 2 mm. The stress is ramped from 1 Pascal up to a stress sufficient to reach a shear rate of approximately 0.1 $\sec^{-1}$.

The ionic cement of the present invention may be selected from any material useful for adhering a dental article to a tooth that cures at least in part through an ionic cement reaction. Such materials are known in a general fashion as two or more part systems used in dentistry. Examples of such materials include zinc phosphate, zinc silicophosphate, zinc oxide-eugenol, zinc polyacrylate, glass ionomers, calcium hydroxide bases, and the like.

Preferred liquids are water and blends of water with solvents or polymerizable liquids. Particularly preferred liquids include a photocurable ionomer, which is defined as a polymer having sufficient pendent ionic groups to undergo a setting reaction in the presence of a reactive filler and water, and sufficient pendent polymerizable groups to enable the resulting mixture to be polymerized, e.g., cured upon exposure to radiant energy.

As noted above, the lyophilic ionic cement component is placed on the dental article as a paste, and then is dried. Advantageously, the lyophilic ionic cement component when in the paste form as applied to the dental article may optionally include a reactive ingredient to initiate the cement reaction. For example, in the case of glass ionomer cements the paste may be comprised primarily of non-reactive solvent, but may optionally contain some glass ionomer polymer or other polymer that would form an extended reticular structure and would tend to bind the powder particles to one another without appreciably reducing the open volume. By carefully controlling either the amount of material that can react with the reactive glass of the lyophilic ionic cement component, or controlling the dwell time of the paste before the lyophilization process is completed, one can generate a partially reacted cement pad that has the desired open volume and still is capable of being reconstituted to a paste form. The resulting pad of cement has greater resistance to breaking or disintegrating as compared to pads not made from pastes containing a small amount of ionomeric polymer or other reactive material. Wetting agents as well as other binders and modifiers could be used in small quantities without interfering with the essential performance of the cement.

Particularly preferred ionic cements used in the present invention comprise photocurable ionomers that contain a polymer having sufficient pendent ionic groups to undergo a setting reaction in the presence of a reactive filler and water, and sufficient pendent polymerizable groups to enable the resulting mixture to be cured by exposure to radiant energy. Examples of such preferred photocurable ionomers are described in U.S. Pat. No. 5,130,347, the disclosure of which is incorporated herein by reference.

The preferred lyophilic ionic cement component is selected from the powder components of glass ionomer cements. These powder components typically include reactive fillers and optionally also include non-reactive fillers. "Reactive fillers," as used herein, refers to a metal oxide or hydroxide, mineral silicate, or ion-leachable glass that is capable of reacting with the ionomer in the presence of water to form a hydrogel. The term "non-reactive filler," as used herein, refers to filler materials that do not react with the ionomer in the presence of water to form a hydrogel.

Reactive fillers suitable for use in the cement systems of this invention include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605, 3,814,717, 4,143,018, 4,209,434, 4,360,605 and 4,376,835.

The reactive filler is preferably a finely divided reactive filler. The filler should be sufficiently finely-divided so that it can be conveniently mixed with the other ingredients and used in the mouth. Preferred average particle diameters for the filler are about 0.2 to about 15 micrometers, more preferably about 1 to 10 micrometers, as measured using, for example, a sedimentation analyzer.

Preferred reactive fillers are acid-reactive. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred. Suitable reactive fillers are also available from a variety of commercial sources familiar to those skilled in the art. For example, suitable fillers can be obtained from a number of commercially available glass ionomer cements, such as "GC Fuji LC" cement and "Kerr XR" ionomer cement. Mixtures of fillers can be used if desired.

If desired, the reactive filler can be subjected to a surface treatment. Suitable surface treatments include acid washing, treatment with phosphates, treatment with chelating agents such as tartaric acid, treatment with a silane or silanol coupling agent. Particularly preferred reactive fillers are silanol treated fluoroaluminosilicate glass fillers, as described in U.S. Pat. No. 5,332,429, the disclosure of which is expressly incorporated by reference herein.

The amount of reactive filler should be sufficient to provide a cement having desirable mixing and handling properties before cure and good cement performance after cure. Preferably, the reactive filler represents less than about 90%, more preferably about 25% to about 85%, and most preferably about 75% to about 85% by weight of the total weight of the cement components.

Non-reactive fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable non-reactive inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable non-reactive organic filler particles include filled or unfilled pulverized polycarbonates, polyepoxides, and the like. Preferred non-reactive filler particles are quartz, submicron silica, and non-vitreous microparticles of the type described in U.S. Pat. No. 4,503,169. Mixtures of these non-reactive fillers are also contemplated, as well as combination fillers made from organic and inorganic materials.

Preferably the surface of the filler particles is treated with a coupling agent in order to enhance the bond between the filler and the polymerizable resin. The use of suitable coupling agents include gamma-methacryloxypropyltrimethoxysilane, gamma-mercaptopropyltriethoxysilane, gamma-aminopropyltrimethoxysilane, and the like.

The cement systems of the invention preferably contain one or more suitable photopolymerization initiators that act as a source of free radicals when activated. Such initiators can be used alone or in combination with one or more accelerators and/or sensitizers.

The photoinitiator should be capable of promoting free radical crosslinking of the ethylenically unsaturated moiety on exposure to light of a suitable wavelength and intensity. It also preferably is sufficiently shelf stable and free of undesirable coloration to permit its storage and use under typical orthodontic conditions. Visible light photoinitiators are preferred. The photoinitiator preferably is water soluble or water miscible. Photoinitiators bearing polar groups usually have a sufficient degree of water solubility or water miscibility. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether(2-methoxy-2-phenylacetophenone), both from Ciba-Geigy Corp.

The photoinitiator should be present in an amount sufficient to provide the desired rate of photopolymerization.

This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

The cement system may also incorporate additional modes of initiation of the polymerization reaction to initiate a crosslinking reaction without the need to expose the cement system to visible light. A preferred additional mode for initiation of the free radical polymerization reaction is the incorporation of an oxidizing agent and a reducing agent as a redox catalyst system to enable the orthodontic composition to cure via a redox reaction. Various redox systems and their use in ionomer cements is described in U.S. Pat. No. 5,154,762, the disclosure of which is expressly incorporated herein by reference. Such two part initiation systems may of course be optionally provided with one part being located in the lyophilic cement component, and the other part being located in the liquid component. Alternatively, the two part initiator system may be mixed together in the liquid at patient chairside immediately before use, or in any other appropriate mixing system.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

Having three cure mechanisms in the glass ionomer system (photocure, dark cure through a redox reaction, and ionic cure) may optionally facilitate thorough, uniform cure and retention of good clinical properties. Cements utilizing threemodes of cure have particular utility in clinical applications where cure of a conventional light-curable composition may be difficult to achieve.

For photocurable ionomers that are polymerized by a cationic mechanism, suitable initiators include salts that are capable of generating cations such as the diaryliodonium, triarylsulfonium and aryldiazonium salts.

Optional other ingredients, such as polymerization initiators, modifying agents and cosolvents can be added at any time and in any manner that does not prematurely begin the setting reaction or the photocuring reaction.

Modifying agents can be used in the cement systems of the present invention in order to provide prolonged working times. Modifying agents useful in the cement system of the present invention are, for example, alkanolamines, e.g., ethanolamine and triethanolamine, and mono-, di- and tri-sodium hydrogenphosphates. Modifying agents can be incorporated into either or both pastes of the present invention. The modifying agents are preferably used at a concentration between about 0.1 to about 10 percent by weight, based on the weight of the reactive filler, and preferably between about 0.5 to about 5 percent.

Cosolvents useful in the present invention include, but are not limited to, low molecular weight organic solvents. Suitable cosolvents include non-copolymerizable organic solvents and copolymerizable low molecular weight hydrophilic alkenyl solvents. The word "copolymerizable" as used herein refers to the ability of the cosolvent to cure compatibly with other polymerizable components that may be used in cements of the invention. Copolymerizable cosolvents can be added to the cement systems of this invention for a variety of reasons, for instance, to provide a homogeneous solution of a photocurable ionomer having inherently low aqueous solubility, to shorten the exposure of radiant energy needed to cure the system, or to vary the physical properties, e.g., the flexibility, of the resultant cured ionomer cement. Examples of suitable cosolvents include non-copolymerizable cosolvents such as ethanol, propanol, and glycerol, and copolymerizable cosolvents such as 2-hydroxylethylmethacrylate or 2-hydroxypropyl-methacrylate.

Optionally, the cement may contain stabilizers. The incorporation of stabilizers serves to further improve the color stability of compositions. Suitable stabilizers include oxalic acid, sodium metabisulfite, metaphosphoric acid, sodium bisulfite, sodium thiosulfate, and combinations thereof. Oxalic acid and sodium metabisulfite are preferred stabilizers.

If desired, the cements of the invention can contain adjuvants such as pigments, inhibitors, accelerators, viscosity modifiers, medicaments and other ingredients that will be apparent to those skilled in the art.

The curing of the ionomer cement system having the capability of being cured through a photoinitiation system is accomplished by exposure to any source of radiant energy capable of causing the desired extent of polymerization of the photocurable ionomer. Suitable radiant energy sources afford a desired combination of such properties as safety, controllability, suitable intensity, and suitable distribution of incident energy. See generally, "Radiation Curing", Kirk-Othmer Encyclopedia of Chemical Technology 3d Ed., Vol. 19, pp. 607–624 (1982). Preferred radiant energy sources are ultraviolet or visible light sources whose emission spectra correspond closely with the absorption range of the polymerization initiator in the ionomer cement system. For instance, sources emitting ultraviolet light at wavelengths between about 335 and 385 nm, and sources emitting visible light in the blue region at wavelengths between about 420 and 480 nm are preferred for use with the preferred ultraviolet- and visible-light-induced polymerization initiators, respectively. For polymerizing cement systems in the mouth, visible light radiation such as that provided by standard dental curing lights is particularly preferred.

Upon exposure of an ionomer cement system of the present invention to an appropriate source of radiant energy, the system rapidly begins to cure, e.g., within about 45 seconds, and preferably within about 30 seconds. The cement generally exhibits the greatest degree of cure near its surface, where the radiant energy is most intense. The surface of the cement therefore can be cured sufficiently to allow subsequent procedures to be performed on the patient, while the interior of the cement is allowed to harden fully by means of the ongoing setting reaction. Thus, if the curing step is omitted, the usual setting reaction will occur, ultimately resulting in the hardening of the material, even in the dark.

The dental article provided with the precoated dental cement as described herein is any article that may appropriately be bonded using an ionic cement system. Examples of such articles include crowns (especially pedo crowns), orthodontic brackets, orthodontic bands, and the like.

In use, a small well is partially filled with the liquid component of the ionic cement. The dental article is next removed from its package or carrier and the lyophilic ionic cement component is partially or completely immersed in the liquid component of the ionic cement. The proper amount of liquid component would be quickly drawn into the pad of cement, which would simultaneously develop the desired consistency of bonding cement. Even in the situation where only one dental article was being bonded, a couple of drops of liquid placed in the well would allow the process to be carried out readily and conveniently without any undue waste of material.

Alternative methods of applying the liquid component of the ionic cement to the lyophilic cement component are also contemplated. For example, the liquid may be applied using a syringe, brush, or other suitable transfer mechanism as will be apparent to those of skill in the art.

Freeze Drying

Equipment: Ace Glass Freeze Drying Apparatus consists of a manifold (P/N 6696-05), collection trap (6696-10), and storage vessels (6696-20). Welch Scientific Vacuum pump. McLeod Gauge. Plastic Dewar flask. Vacuum tubing.

Procedure: The plastic Dewar is used for an isopropyl alcohol/dry ice bath for the collection trap. The storage vessels are chilled in separate liquid nitrogen baths. The samples to be freeze dried are submerged in liquid nitrogen for a few seconds (or cooled in the atmosphere above liquid nitrogen) and then they are placed in the storage vessels that are then attached to the manifold of the freeze dry apparatus. After all vessels are in place, the vacuum pump is started. Pumping continued until the samples appear to be dry and the pressure (McLeod Gauge) is less than 0.5 Torr. (Preferably, the vacuum is run about one-half hour to one hour, until all frost and moisture have evaporated from the vessels, and they do not feel cool to the touch).

Pastes are prepared by mixing pure solvents or solutions of polymers with powder constituents, e.g., zinc oxide or powdered glass. The resulting pastes are placed in a syringe that is used to apply material to the bonding base of orthodontic brackets. Sufficient material is applied so that it would be adequate to bond to teeth, allowing a slight excess to exude around the base after being pressed in place on the tooth surface. The bracket having paste applied thereto are placed in a test tube or beaker, which is held in liquid nitrogen for about five seconds and then placed in the freeze dry vessel. After the samples are freeze dried, the base of the bracket is dipped into the liquid portion of a light cure glass ionomer cement, e.g., Fuji Ortho LC Liquid, and then placed on a tooth surface. The sample is then exposed to a visible light curing device for twenty seconds (ten seconds from each side).

Band Shear Strength Test Procedure

Orthodontic molar bands that have been modified by welding on four lugs on the occlusal edge were used in this testing. The molar bands are filled with banding cement and then mounted on cylindrical test mandrels. Excess cement is removed and the test pieces are stored in 37° C. test chamber over water. After overnight storage, the samples are tested on an Instron Universal Testing Machine. The test mandrel is held in place in the lower portion of the apparatus, and a gripping device is placed on the band so that it engages the lugs and applies a shear force when the crosshead is moved upward. A crosshead speed of 0.5 in/min was used for testing.

Bracket Shear Strength Test Procedure

Standard bond strength testing is performed on bovine teeth as test substrates. Bovine teeth are cut from calf jaws and mounted in cold cure acrylic cylinders. The teeth are pumiced just prior to testing to clean the enamel. Pumicing is done using a horse hair wheel and slurry of pumice. After pumicing, the teeth are thoroughly rinsed in water. Brackets were bonded to the teeth as described in the various examples. The samples were placed in water and stored at 37±2° C. overnight (16 to 24 hours). The specimens are mounted on an Instron Universal Testing Machine for determination of bond strength. Specimens are placed so that force is applied to the occlusal edge of the bracket. A round stainless steel wire (0.016 to 0.022) is gripped in the upper jaw of the test machine and looped around the tie wings. A crosshead speed of 0.2 in/min is used for standard testing. The force to debond the bracket in a peel/shear mode is recorded on the instrument chart paper or a computer.

The present invention will be further understood in view of the following examples which are merely illustrative and not meant to limit the scope of the invention. Unless otherwise indicated, all parts and percentages are by weight.

Experimental

The adhesives of this type are comprised of (1) glass powder, (2) polycarboxylic acid, (3) hydroxyethylmethacrylate (HEMA) and (4) water. In addition there are thermal and light activated free radical generators.

There are as many as three mechanisms that participate in the adhesive cure. the combination of water, glass powder and polycarboxylic acid causes cations to leach from the glass and irreversibly combine with the polycarboxylic acid. This is the standard glass ionomer (GI) cure. The thermal free radical cure occurs when the initiator and free radical generator are combined. The light cure chemicals can be pre-mixed but must be shielded from light to prevent initiation of the free radical cure. The adhesive formulations all must accommodate the stability of the uncured adhesive and the avoidance of premature curing.

EXAMPLES 1–5

The first step is to mix the glass with a volatile (sublimable) solvent. In the case of water, a certain level of reaction will take place in which the cations that facilitate the ionomer reaction will be leached out. If there is ionomer present a certain level of cure will take place with the benefit of giving structural integrity to the pad of glass powder following freeze-drying. If ethanol or equivalent solvent is used there will be minimal extraction of cations from the glass and the polymer present will remain essentially unreacted until activated by the addition of water. Using mixtures of water and other solvents such as ethanol will allow intermediate levels of precure by way of the GI reaction.

| EX. NO. | GLASS POWDER (gm) | SOLVENT (Type, Amt) | POLYMER | HEMA/H$_2$O | CURATIVES |
|---|---|---|---|---|---|
| 1 | 0.9 | 0.6 gm, 1% PAA in water | 50% PAA | 20%/30% | — |
| 2 | 0.9 | 0.6 gm, 2% alginate in water | 50% PAA | 20%/30% | — |
| 3 | 0.9 | 0.6 gm, 0.5% PAA & 1.0% alginate | 50% PAA | 20%/30% | — |
| 4 | 0.95 | 0.68 gm VB copolymer in isopropanol | 25% VB copolymer slurry | 40%/60% | — |
| 5 | 1.2 | 0.9 gm EtOH (absolute) | 33% VB copolymer solution | 20%/30% | 2% DPI 0.4% CPQ |

VB is the copolymer as described in Example 11 of U.S. Pat. No. 5,130,347, the disclosure of which is incorporated herein by reference. PAA is polyacrylic acid as sold by GC Corporation in GC "Ortho" conditioner. In each experiment the powder slurry was applied to the base of a metal bracket. The bracket was then cooled using liquid nitrogen until the solvent was completely frozen. It was next placed in a freeze drying apparatus and kept frozen while the pressure was lowered to less than one Torr. It was held frozen under vacuum until all of the solvent had sublimed. The pad of powder on the bracket base had an opaque white appearance. It was subsequently touched to the water resin mixture according to the above table whereupon the liquid was drawn into the pad of powder changing instantly to a powder/liquid paste. It was immediately applied to a wet tooth that had been maintained submersed in water. The bracket was pressed into place until excess adhesive exuded form the periphery whereupon the curing light was directed toward each of the four sides for a total of 40 seconds. The bracket in each case was rigidly attached to the tooth with greater than 10 pounds of force required to remove it.

Freeze Dry Examples

EXAMPLE 6

0.90 grams of 3M Unitek glass ionomer powder mixed with 0.63 grams of a solution of 10% Vitrebond copolymer in distilled water. This mixture was applied to the bonding base of metal mesh brackets and then freeze dried vacuum ½ hour until room temperature (frost is gone) after immersion of a vessel in liquid nitrogen. The sample was then dipped in a solution of 60/40 water/HEMA that contained 20% Vitrebond (VB) copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 5, 7, and 18 pounds were measured.

EXAMPLE 7

0.90 grams of 3M Unitek glass ionomer powder mixed with 0.52 grams of a solution of 10% Vitrebond copolymer in isopropyl alcohol. This mixture was applied to the bonding base of metal mesh brackets and then freeze dried after immersion in liquid nitrogen. The sample was then dipped in a solution of 60/40 water/HEMA that contained 20% Vitrebond copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 20, 17, and 10 pounds were measured.

EXAMPLE 8

0.90 grams of 3M Unitek glass ionomer powder mixed with 0.53 grams of a slurry of 10% Vitrebond copolymer in t-butyl alcohol. This mixture was applied to the bonding base of metal mesh brackets and then freeze dried after immersion in liquid nitrogen. The sample was then dipped in a solution of 60/40 water/HEMA that contained 20% Vitrebond copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 9, 35, and 37 pounds were measured. This experiment was repeated using 0.90 grams of powder and 0.50 grams of liquid. Bond strengths of 29, 30, 30, 14 and 16 pounds were measured.

EXAMPLE 9

0.96 grams of Ormco PROTECH® Gold glass ionomer band cement powder mixed with 0.53 grams of a slurry of 10% Vitrebond copoly in t-butylalcohol. This mixture was applied to the bonding base of metal mesh brackets and then freeze dried after immersion in liquid nitrogen. The sample was then dipped in a solution of Ormco PROTECH liquid that had been diluted 50/50 (w/w) with distilled water. The brackets were mounted on unetched bovine teeth by pressing into place. The samples were stored overnight in 37° C. water. Bond strengths of 11 and 5 pounds were measured.

EXAMPLE 10

0.96 grams of Espe DURELON® cement powder mixed with 0.45 grams of a slurry of 10% Vitrebond copolymer in t-butylalcohol. This mixture was applied to the bonding base of metal mesh brackets and then freeze dried after immersion in liquid nitrogen. The sample was then dipped in a solution of DURELON liquid that had been diluted 50/50 (w/w) with distilled water. The brackets were mounted on unetched bovine teeth by pressings ionomernto place. The samples were stored overnight in 37° C. water. Bond strengths of 26 and 21 pounds were measured.

EXAMPLE 11

0.95 grams of milled glass (fluoroaluminosilicate)powder mixed with 0.50 grams of a solution of 10% Vitrebond copolymer in isopropyl alcohol. This mixture was applied to the bonding base of metal mesh brackets and then freeze dried after immersion in liquid nitrogen. The sample was then dipped in a solution of 60/40 water/HEMA that contained 20% Vitrebond copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 19, 16, and 8 pounds were measured.

EXAMPLE 12

0.95 grams of milled glass (fluoroaluminosilicate) powder mixed with 0.50 grams of a slurry of 10% Vitrebond copolymer in t-butyl alcohol. This mixture was applied to the bonding base of metal mesh brackets and then freeze dried after immersion in liquid nitrogen. The sample was then dipped in a solution of 60/40 water/HEMA that contained 20% Vitrebond copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 7, 7, and 14 pounds were measured.

Air Dried Examples

EXAMPLE 13

0.90 grams of 3M Unitek glass ionomer powder mixed with 0.52 grams of a solution of 10% Vitrebond copolymer in isopropyl alcohol. This mixture was applied to the bonding base of metal mesh brackets and then air dried. The sample was then dipped in a solution of 60/40 water/HEMA that contained 20% Vitrebond copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 7 and 15 pounds were measured.

EXAMPLE 14

0.95 grams of milled glass (fluoroaluminosilicate) powder mixed with 0.50 grams of a slurry of 10% Vitrebond copolymer in t-butyl alcohol. This mixture was applied to the bonding base of metal mesh brackets and then air dried. The sample was then dipped in a solution of 60/40 water/ HEMA that contained 20% Vitrebond copolymer, 1.6% diphenyl iodonium hexafluorophosphate salt and 0.32% CPQ. The brackets were mounted on unetched bovine teeth by pressing into place and then exposing the bracket to an Ortholux Curing Light for 20 seconds (10 seconds on each side). Bond strengths of 7, 10, and 12 pounds were measured.

Banding Examples

EXAMPLE 15

2.03 grams of Ormco PROTECH glass ionomer band cement powder were mixed with 1.25 grams of a slurry of 10% Vitrebond copolymer in t-butyl alcohol. This mixture was applied to the inner surface of orthodontic molar bands that were then exposed to liquid nitrogen and then freeze dried. The treated bands were immersed in a 50/50 (w/w) solution of PROTECH liquid and distilled water. The bands were then seated on a banding test fixture and stored overnight over 37° C. water. The band strength was measured by pulling off the band in shear at 0.5 in./min. The measured forces were 12, 31, and 35 pounds. This compares to similar bands cemented with Ormco PROTECH cement mixed according to the manufacturer's instructions that had forces of 35 and 35 pounds.

EXAMPLE 16

2.18 grams of Espe DURELON zinc oxidepowder were mixed with 1.23 grams of a slurry of 10% Vitrebond copolymer in t-butyl alcohol. This mixture was applied to the inner surface of orthodontic molar bands that were then exposed to liquid nitrogen and then freeze dried. The treated bands were immersed in a 50/50 (w/w) solution of DURELON liquid and distilled water. The bands were then seated on a banding test fixture and stored overnight over 37° C. water. The band strength was measured by pulling off the band in shear. The measured forces were 7 and 18 pounds. This compares to similar bands cemented with Espe DURELON cement mixed according to the manufacturer's instructions that had forces of 42, 57, and 94 pounds.

EXAMPLE 17

2.37 grams of 3M Unitek BLEND-EZE® Zinc Phosphate powder were mixed with 1.10 grams of a slurry of 10% Vitrebond copolymer in t-butyl alcohol. This mixture was applied to the inner surface of orthodontic molar bands that were then exposed to liquid nitrogen and then freeze dried. The treated bands were immersed in BLEND-EZE liquid. The bands were then seated on a banding test fixture and stored overnight over 37° C. water. The band strength was measured by pulling off the band in shear. The measured forces were 10 and 19 pounds. This compares to similar bands cemented with 3M Unitek BLEND-EZE mixed according to the manufacturer's instructions that had forces of 48, 88, and 91 pounds.

What is claimed is:

1. A system comprising
    a dental article,
    a dry porous pad of lyophilic ionic cement component on at least one surface of the dental article, and
    a liquid;
    wherein the cement component is capable of being cured through polymerization reaction.

2. The system according to claim 1 wherein the dry porous pad is freeze-dried.

3. The system according to claim 1 wherein the dry porous pad comprises a reactive glass ionomer cement.

4. The system according to claim 1 wherein the dry porous pad is a portion of a zinc phosphate cement.

5. The system according to claim 1 wherein the dry porous pad is a portion of a zinc-oxide-eugenol cement.

6. The system according to claim 1 wherein the dry porous pad is a portion of a zinc polyacrylate cement.

7. The system according to claim 1 wherein the dry porous pad is a portion of a calcium hydroxide base cement.

8. The system according to claim 1 wherein the dry porous pad comprises a photocurable ionomer.

9. The system according to claim 1, wherein the dry porous pad is capable of absorbing between about 10–130% of its weight of liquid after 5 seconds of total immersion of the dry porous pad in the liquid.

10. The system according to claim 1, wherein the dry porous pad is capable of absorbing between about 20–110% of its weight of liquid after 5 seconds of total immersion of the dry porous pad in the liquid.

11. The system according to claim 1, wherein the dry porous pad is capable of absorbing between about 30–90% of its weight of liquid after 5 seconds of total immersion of the dry porous pad in the liquid.

12. The system according to claim 1, wherein the article is an orthodontic bracket.

13. The system according to claim 1, wherein the article is an orthodontic molar band.

14. The system according to claim 1, wherein the article is a dental crown.

15. A method for adhering a dental article to a tooth or teeth, comprising:
   a) providing a system according to claim 1;
   b) contacting the dry porous pad of lyophilic ionic cement component to the liquid, thereby forming a cement paste;
   c) pressing the cement paste to the tooth; and
   d) allowing a cement reaction to occur, thereby adhering the article to the tooth or teeth.

16. The method according to claim 15, wherein the article is an orthodontic bracket.

17. A process for manufacture of a dental article having a dry porous pad of lyophilic ionic cement component on at least once surface of the article comprising:
   a) forming a paste from components of an ionic cement and a solvent
   b) applying the paste to a surface of an dental article; and
   c) allowing the paste to dry to form a dry porous pad of lyophilic ionic cement component.

18. The process of claim 17, wherein the paste is freeze-dried on the article.

19. The process of claim 17, wherein the solvent is selected from the group consisting of water, ethanol, isopropanol, and t-butanol.

20. The process of claim 17, wherein the article is an orthodontic bracket.

21. The product made by the process of claim 17.

* * * * *